US006505063B2

(12) United States Patent
Van Den Brink et al.

(10) Patent No.: US 6,505,063 B2
(45) Date of Patent: Jan. 7, 2003

(54) DIAGNOSTIC IMAGING SYSTEM WITH ULTRASOUND PROBE

(75) Inventors: Johan Samuel Van Den Brink, Eindhoven (NL); Frederik Visser, Eindhoven (NL); Michael Harald Kuhn, Hamburg (DE)

(73) Assignee: Koninklijke Philips Electronics N.V., Eindhoven (NL)

(\*) Notice: Subject to any disclaimer, the term of this patent is extended or adjusted under 35 U.S.C. 154(b) by 0 days.

(21) Appl. No.: 09/736,014

(22) Filed: Dec. 13, 2000

(65) Prior Publication Data

US 2002/0128550 A1 Sep. 12, 2002

(30) Foreign Application Priority Data

Dec. 15, 1999 (EP) .............................................. 99204329
Jul. 21, 2000 (EP) .............................................. 00202642

(51) Int. Cl.⁷ ................................................ A61B 5/00
(52) U.S. Cl. ........................ 600/411; 382/131; 600/443; 600/408; 128/922
(58) Field of Search ................................ 600/407, 410, 600/414, 424, 439, 446, 459, 427, 408, 443; 128/920, 916, 922; 382/128, 131; 606/130

(56) References Cited

U.S. PATENT DOCUMENTS

| 4,543,959 A | | 10/1985 | Sepponen ................... 128/653 |
| 4,951,653 A | \* | 8/1990 | Fry et al. ..................... 600/411 |
| 5,146,924 A | | 9/1992 | Seepponen ............... 128/653.2 |
| 5,619,999 A | \* | 4/1997 | Von Behren et al. ....... 600/445 |
| 5,633,951 A | | 5/1997 | Moshfeghi .................. 382/154 |
| 5,662,109 A | \* | 9/1997 | Hutson ........................ 600/411 |
| 5,961,454 A | \* | 10/1999 | Kooy et al. .................. 600/407 |
| 6,016,439 A | \* | 1/2000 | Acker .......................... 600/411 |
| 6,094,590 A | \* | 7/2000 | Kan et al. .................... 600/411 |
| 6,216,029 B1 | \* | 4/2001 | Paltieli ........................ 600/411 |
| 6,248,074 B1 | \* | 6/2001 | Ohno et al. ................. 128/916 |
| 6,317,617 B1 | \* | 11/2001 | Gilhuijs et al. ............. 128/922 |
| 6,390,982 B1 | \* | 5/2002 | Bova et al. .................. 128/916 |

FOREIGN PATENT DOCUMENTS

EP 09024034 7/1995 ........... A61B/5/055

OTHER PUBLICATIONS

"Fast Calibration for 3D Ultrasound Imaging and Multimodality Image Resigration" by N. Pagoulatos, D.R. Haynor, and Y. Kim in Proceedings fo the first Joint BMES/EMBS Conference Serving Humanity, Advancing Technology, Oct. 13–16, 1999, Atlanta, GA, pp. 1065, vol. 2.

\* cited by examiner

Primary Examiner—Marvin M. Lateef
Assistant Examiner—Eleni Mantis Mercader
(74) Attorney, Agent, or Firm—John Vodopia

(57) ABSTRACT

A diagnostic imaging system, notably a magnetic resonance imaging system comprises a receiver antenna for picking-up magnetic resonance signals and an ultrasound probe for receiving ultrasound echoes. A reconstruction unit is arranged to reconstruct a diagnostic image from the magnetic resonance signals and the ultrasound echoes in particular, the magnetic resonance image and ultrasound images are registered in a common reference frame and geometric distortions in the ultrasound image are corrected on the basis of the magnetic resonance image. Different tissues types are distinguished in the magnetic resonance image and corrections are made for differences between ultrasound sound velocities in these tissue types. Further, information contained in the magnetic resonance signals can be displayed in combination in the ultrasound echoes.

11 Claims, 2 Drawing Sheets

DIAGNOSTIC IMAGING SYSTEM WITH ULTRASOUND PROBE

BACKGROUND OF THE INVENTION

The invention relates to a diagnostic imaging system, in particular a magnetic resonance imaging system which is provided with an ultrasound probe.

Such a magnetic resonance imaging system is known from the U.S. Pat. No. 5,146,924.

The known magnetic resonance imaging system comprises a receiver antenna for receiving magnetic resonance signals which is mounted in an ultrasound transducer. The ultrasound transducer includes an ultrasound source for generating ultrasound waves in the object to be examined, such as a patient who is to be examined. The ultrasound transducer also includes the ultrasound probe. The ultrasound probe detects ultrasound echoes, i.e. ultrasound waves which are reflected in an object to be examined. The central processor of the known magnetic resonance imaging system derives from the detected ultrasound waves an ultrasound image of a part of the object to be examined. From this ultrasound image the user determines the position of the part of the anatomy to be examined, notably the organ of interest. Subsequently, on the basis of the position of the part to be examined as detected from the ultrasound image, there are excited (nuclear) spins in the object to be examined of the part to be examined upon which excitation magnetic resonance signals are generated and a magnetic resonance image of the part to be examined is reconstructed from the magnetic resonance signals. The known magnetic resonance system employs the 'Overhauser'-effect to generate the magnetic resonance image. The known magnetic resonance imaging system employs the ultrasound image only for the determination of the position of the part of the object of which a magnetic resonance image is made.

SUMMARY OF THE INVENTION

An object of the invention is to provide a diagnostic system which is suitable to supply diagnostic image with a higher diagnostic quality, notably having a higher diagnostic information content.

This object is achieved by the diagnostic imaging system which, according to the invention comprises a reconstruction unit for reconstructing a diagnostic image from the magnetic resonance signals and the ultrasound echoes.

The magnetic resonance signals are generated by RF-excitation of (unclear) spins in the object which is placed in a stationary magnetic field. Temporary magnetic gradient fields are applied so that the Larmor frequency of the excited spins is made spatial position dependent. Thus, spatial encoding of the magnetic resonance signals by the frequencies and phases of the magnetic resonance signals is achieved.

The diagnostic image combines image information both from the magnetic resonance signals and from the ultrasound echoes. For example the diagnostic image includes a portion of pixels that are derived from the magnetic resonance signals and another portion of pixels that are derived from the ultrasound echoes. The information included in the magnetic resonance signals has a high spatial resolution but a low temporal resolution. On the other hand, the information included in the ultrasound echoes has a lower spatial resolution but a much higher temporal resolution. In particular the information in the magnetic resonance signals is time-averaged over a range of about 50 ms to about 0.5 s and the information in the ultrasound echoes pertains to short periods of time of about 5–20 ms. The information in the magnetic resonance signals may have a high spatial resolution in that details as small as 0.5 mm are faithfully represented in the magnetic resonance image. The diagnostic image thus combines image information with a high spatial resolution with image information with a high temporal resolution. Thus, the diagnostic image shows in particular image information of high temporal resolution of rapidly moving parts in the patient to be examined while the anatomical surroundings of the rapidly moving portions are accurately displayed with a high spatial resolution. For example, moving portions of the patient's heart are displayed against the correctly spatially highly resolved anatomical background.

In another example, the diagnostic image combines functional information from the ultrasound echoes of the reconstruction which is displayed in the anatomical information from the magnetic resonance signals. For example, in the diagnostic image colour-Doppler values derived from the ultrasound echoes may replace grey-values derived from the magnetic resonance signals.

These and other aspects of the invention will be elaborated with respect to the preferred embodiments as defined in the dependent Claims.

In a preferred embodiment the reconstruction unit is arranged to derive a magnetic resonance image and a preliminary ultrasound image from the magnetic resonance signals and the ultrasound echoes, respectively. The diagnostic image may be derived from the magnetic resonance image and the preliminary ultrasound image. The term 'preliminary ultrasound image' in this application indicates any ultrasound image to which correction on the basis of the magnetic resonance image or registration relative to the magnetic resonance image is still to be performed. For example, respective portions of the preliminary ultrasound image and of the magnetic resonance image are included into the diagnostic image. In an other example, the diagnostic image is formed in that at least respective portions of the magnetic resonance image and the preliminary ultrasound image are displayed alternatingly.

In a further preferred embodiment, the magnetic resonance image and the preliminary ultrasound image are registered in a common co-ordinate system. That is, between respective positions in the magnetic resonance image and in the preliminary ultrasound image the geometric relation is established. On the basis of this geometric relation positions in the magnetic resonance image and in the ultrasound image are registered in correspondence with the geometric relation between the imaged positions in the object. This may be achieved by relating positions in the preliminary ultrasound image an in the magnetic resonance image to a common reference frame. Such a common reference system is for example defined in the examination room in which the diagnostic imaging system is set up. Notably, a position detection system is provided in the examination room. The position detection system measures the positions of the ultrasound probe relative to the patient to be examined. The position detection system also determines the geometric relation between positions in the patient to corresponding positions in the magnetic resonance image. The position detection system may include an optical or acoustical position detection system which measures the positions of the patient and the ultrasound probe. The position of the ultrasound probe determines a region, in particular a slice, of the patient from which the ultrasound echoes are received. Thus, from the measurement of the position of the ultrasound probe, the part imaged in the preliminary ultrasound image is established. Notably, when an optical position detection system is employed, the ultrasound probe and the patient are fitted with light-emitting diodes (LEDs) or infrared-emitting diodes (IREDs). The radiation, notably light or infrared radiation, from the LEDs or IREDs is detected from two or more directions by means of a camera-unit. The camera-unit picks up images from the sets of LEDs or IREDs. The diagnostic imaging system comprises a computer which is also programmed to derive the position of the ultrasound probe relative to the patient from the image picked-up by the camera-unit of the LEDs or IREDs. The gantry of the magnetic resonance imaging system is preferably also fitted with LEDs or IREDs and the camera-unit further picks-up images of the MR-gantry, notably these images also feature images of the LEDs or IREDs on the MR-gantry. The computer is also arranged to calculate the position of the gantry relative to the patient to be examined. Further, the computer is arranged to compute the geometric relation between positions in the patient and the corresponding positions in the magnetic resonance image on the basis of the measured relative position of the patient to the MR-gantry and on the basis of the applied temporary magnetic gradient fields, such as the slice selection, phase encoding and read-out gradients. Thus it is achieved to establish the geometric relationship between corresponding positions in the magnetic resonance image and in the preliminary ultrasound image. The magnetic resonance image and the preliminary ultrasound image are registered in a common co-ordinate system which is based on the geometric relation between the magnetic resonance image and the preliminary ultrasound image. In this respect, corresponding positions in either image pertain their common position in the patient. As the magnetic resonance image and the preliminary ultrasound image are registered in the common co-ordinate system the diagnostic image which is derived from the magnetic resonance image and the preliminary ultrasound image shows image information from the magnetic resonance image and from the preliminary ultrasound image in their correct mutual geometric relation. That is, e.g. respective portions of the preliminary ultrasound image and of the magnetic resonance image are included in the diagnostic image at correct relative positions to one another.

In a preferred embodiment of the diagnostic system according to the invention the magnetic resonance image is employed to correct the preliminary ultrasound image and form the diagnostic image as the corrected ultrasound image. The diagnostic image may also be formed by combining portions if the corrected ultrasound image and the magnetic resonance image. Notably, the magnetic resonance image can be used to correct geometric distortions in the preliminary ultrasound image. For example, portions in the ultrasound image relating different tissue types are distinguished on the basis of the magnetic resonance image. For example, local ultrasound sound velocities for such different tissue types are derived from the magnetic resonance image and the preliminary ultrasound image is corrected for distortions due to differences between ultrasound sound velocities. Further, tissue interfaces can be located in the magnetic resonance image and related to US-echoes from these tissue interfaces so that renditions of tissue interfaces in the magnetic resonance image and in the corrected ultrasound image are in correspondence.

In a preferred more simple embodiment of the diagnostic imaging system corresponding anatomical landmarks are identified in the magnetic resonance image and in the preliminary ultrasound image. From the respective positions of the anatomical landmarks in the magnetic resonance image and correspondingly in the preliminary ultrasound image the correct geometric relation between corresponding positions in the preliminary ultrasound image and in the magnetic resonance image are calculated. On the basis of the geometric relation based on the corresponding anatomical landmarks, the preliminary ultrasound image and the magnetic resonance image are registered in the common co-ordinate system. From these registered preliminary ultrasound image and the registered magnetic resonance image the diagnostic image is formed.

In another embodiment of the diagnostic image according to the invention the position of the ultrasound probe is measured on the basis of the magnetic resonance signals. Notably, at least a part of the magnetic resonance signals picked-up by the receiver antenna relates to or originates from the ultrasound probe, e.g. the ultrasound probe or markers having a substantial magnetic susceptibility being fitted to the ultrasound probe are also imaged in the magnetic resonance image. Thus, from the position of the ultrasound probe as measured on the basis of the magnetic resonance signals the geometric relation between the ultrasound probe and thus the preliminary ultrasound image and the magnetic resonance image is obtained. On the basis of this geometric relation the preliminary ultrasound image and the magnetic resonance image can be registered in the common co-ordinate system and the diagnostic image formed on the basis of the registered preliminary ultrasound image and the registered magnetic resonance image.

In another embodiment the ultrasound probe is fitted with micro-coils. While the magnetic resonance signals are generated the micro-coils pick-up a part of the magnetic resonance signals form the close neighbourhood of the micro-coils. Thus the magnetic resonance signals picked-up by the micro-coils represent the position of the ultrasound probe. The micro-coils produce electrical (induction) signals in response to the magnetic resonance signals. These electrical signals in turn represent the position of the ultrasound probe relative to the patient and relative to the MR-gantry. These electrical signals from the micro-coils are advantageously employed to determine the geometric relation between the preliminary ultrasound image derived from the ultrasound echoes picked-up by the ultrasound probe and the magnetic resonance image.

The functions of the diagnostic imaging system are in practice performed under the control of a computer programme including various instructions which enable the diagnostic imaging system to produce the technical effects involved in the present invention. Such a computer programme is loaded into e.g. the working memory or accessible to the processor of e.g. a control unit and/or a reconstruction unit or combination unit of the diagnostic imaging system. The computer programme may be made available on a data carrier such as a CD-ROM disk, or the computer programme may be downloaded from a network, such as the world-wide web.

Another object of the invention is to provide a magnetic resonance imaging system which also enables the acquisition of information which relates to current instants or very short periods of time.

This further object is achieved by means of a magnetic resonance imaging system according to the invention which is provided with a display system for the combined display of information contained in the magnetic resonance signals and information contained in the ultrasound waves.

The display system includes inter alia a signal processing unit and a monitor. An LCD (liquid crystal) monitor is suitable for use in combination with the magnetic resonance imaging system, because such an LCD monitor is not very sensitive to the magnetic (temporary) gradient fields necessary to generate and receive the magnetic resonance signals. The LCD monitor is preferably electromagnetically shielded from the magnetic resonance imaging system in order to prevent the electronic signals controlling the LCD monitor from disturbing the acquisition of the magnetic resonance signals and to prevent the magnetic resonance signals from disturbing the control of the LCD monitor. The signal processing unit is arranged to reconstruct a magnetic resonance image from the magnetic resonance signals and also to form an ultrasound image on the basis of the detected ultrasound waves. The detected ultrasound waves have notably been reflected as ultrasound echoes in the object to be examined. The magnetic resonance signals are detected by means of the receiver antenna, such as a receiver coil, so as to be applied to the signal processing unit. The ultrasound waves are detected by the ultrasound probe. The ultrasound probe produces US detection signals in response to the detected ultrasound waves. The US detection signals represent the information contained in the ultrasound waves; for example, the signal levels of the US detection signals correspond to the strengths of the ultrasound waves. The US detection signals are also applied to the signal processing unit. The magnetic resonance image and the ultrasound image are both represented by image signals in the signal processing unit, for example, electronic video signals. These image signals are applied to the monitor so that the image information contained in the magnetic resonance signals and in the ultrasound waves is visualized.

In conformity with the invention the display system displays the magnetic resonance image and the ultrasound image in combined form on the monitor. The ultrasound image contains mainly instantaneous information, or at least information relating to very short periods of time, i.e. periods of time shorter than the time typically required for the acquisition of the magnetic resonance signals for the magnetic resonance image; these short periods of time notably have a duration of from approximately 5 to 20 ms. The period of time over which averaging effectively takes place during the formation of the magnetic resonance image is dependent on the spiral resolution of the magnetic resonance image and on the exact acquisition strategy used to sample the k space. It has been found in practice that the period of time over which the information in the magnetic resonance image is averaged amounts to from approximately 50 ms to some tenths of a second. Combined display of the ultrasound image and the magnetic resonance image provides information concerning instantaneous events in the object to be examined, for example a patient to be examined, together with the time averaged, but spatially suitably resolved information. This is because, generally speaking, the magnetic resonance image has a spatial resolution which is higher than that of the ultrasound image. Due to the combined display, the information of high spatial resolution from the magnetic resonance image can b combined with information of high temporal resolution from the ultrasound image. The magnetic resonance image contains information which has been averaged in time to a given extent. Due to the combined display of the ultrasound image and the magnetic resonance image, information concerning instantaneous events in the object to be examined, for example a patient to be examined, can be made available together with time averaged information.

The ultrasound image contains, for example, mainly functional information concerning physical processes taking place in the object to be examined. For example, quantities which quantify the flow of a liquid, for example, blood through the blood vessels of the patient to be examined, are concerned. The magnetic resonance imaging system according to the invention enables the reproduction of such functional information contained in the ultrasound image in, for example, the magnetic resonance image. The magnetic resonance image preferably reproduces with a high spatial resolution the anatomical structure of the patient to be examined. The radiologist is thus offered a good quantitative image of the functional information and also a suitably spatially resolved image of the region wherefrom the functional information originates.

The combined display of the magnetic resonance image and the ultrasound image can be realised in various ways. For example, there is formed a composite image with partly brightness values from the magnetic resonance image and partly brightness from the ultrasound image. It is alternatively possible to alternate the magnetic resonance image and the ultrasound image. For example, the magnetic resonance image and the ultrasound image alternate at a rate of approximately 20 fps (frames per second). Furthermore, it is also possible to superpose the ultrasound image as an "overlay" on the magnetic resonance image.

For example, grey values in the magnetic resonance image are replaced by colour Doppler values from the ultrasound image.

The magnetic resonance image as well as the ultrasound image can represent the distribution of the values of a physical quantity. For example, the physical quantity concerns perfusion or flow of a fluid of physiological importance. For example, cerebrospinal fluid (CSF) or arterial or venous blood are concerned. According to the invention the spatial distribution of physical quantities derived from physical quantities represented by the magnetic resonance image and by the ultrasound image can be reproduced in the composite image. For example, the combined image can reproduce the spatial distribution of the ratio of peak flow values and local mean flow values.

The reconstruction unit is preferably arranged to register the magnetic resonance image and the ultrasound image in a common reference system. For example, this can be realised by identification of corresponding anatomical details in the magnetic resonance image and in the ultrasound image. It is also possible to measure the position of the ultrasound probe by means of the magnetic resonance imaging system; to this end, the ultrasound probe is preferably provided with one or more identification members which are susceptible to the RF excitation. For example, microcoils are suitable identification members. Due to the RF excitations, the microcoils receive magnetic resonance signals which represent the position of the microcoils and hence of the ultrasound probe. The magnetic resonance image and the ultrasound image are registered in the common reference system on the basis of the measured position of the ultrasound probe. On the basis of the temporary (for example, read-out and phase encoding) gradient fields the magnetic resonance imaging system determines the position of the ultrasound probe as well as the position of the part of the object being imaged in the magnetic resonance image.

It is noted that advantageously according to the invention the correction of the (preliminary) ultrasound image and the registration of the (preliminary) ultrasound image may also be employed to correct and/or mutually register highly spatially resolved information of the magnetic resonance image and highly temporally resolved image information in the (preliminary) ultrasound image.

BRIEF DESCRIPTION OF THE DRAWINGS

These and other aspects will be elaborated in more detail and by way of example with respect to the embodiments discussed hereinafter and with respect to the appended drawings wherein.

DESCRIPTION OF THE PREFERRED EMBODIMENTS

Figure 1:
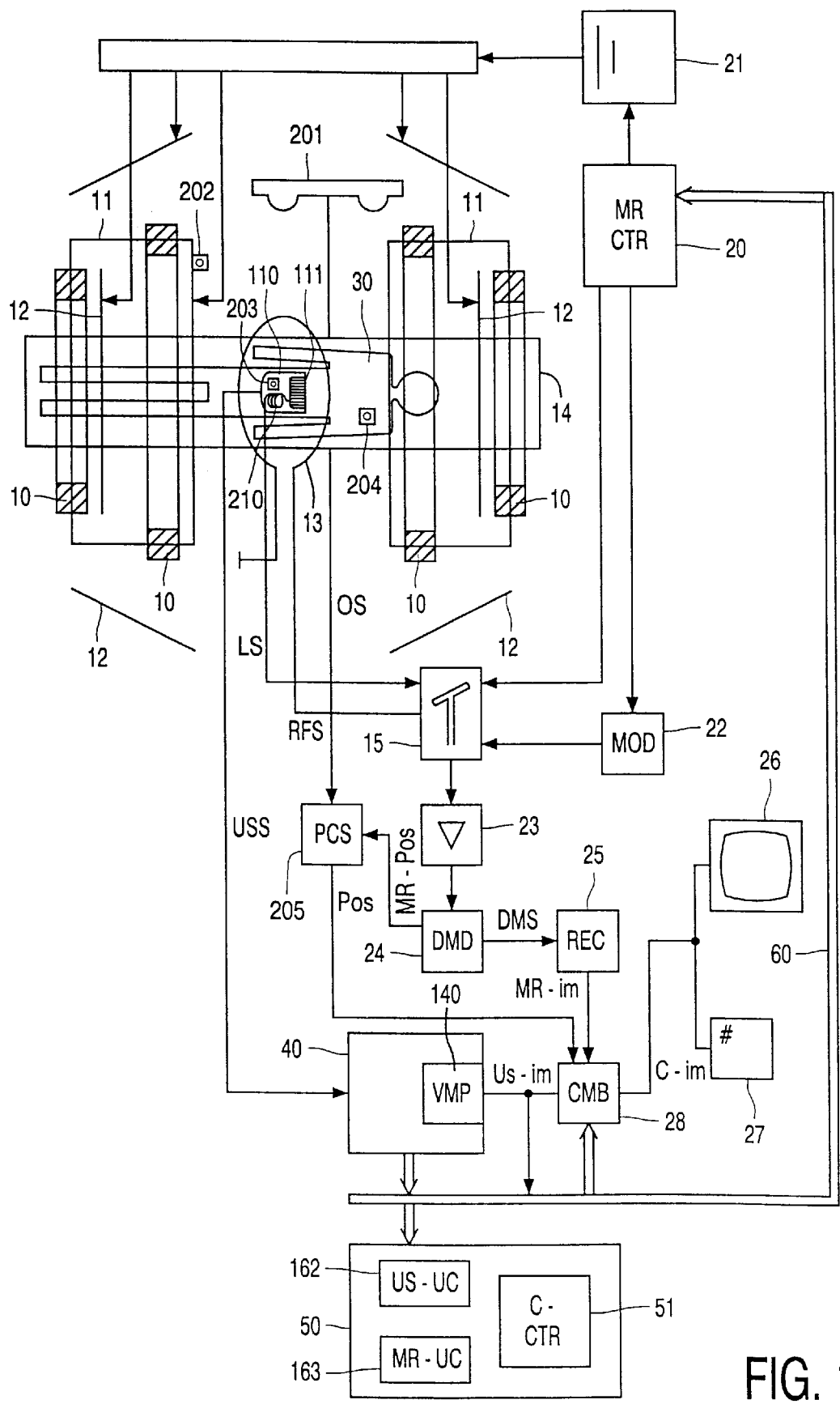
FIG. 1 shows diagrammatically a magnetic resonance imaging system in which the invention is used.

FIG. 1 shows diagrammatically a diagnostic imaging system in which the invention is used. The magnetic resonance imaging system is provided with a set of main coils 10 which generate the steady, uniform magnetic field. The main coils are constructed, for example, in such a manner that they enclose a tunnel-shaped examination space in which the magnetic field prevails. The patient to be examined is moved into this tunnel-shaped examination space. The magnetic resonance imaging system also includes a number of gradient coils 11, 12 whereby magnetic fields with spatial variations, notably in the form of temporary gradients in separate directions, are superposed on the uniform magnetic field. The gradient coils 11, 12 are connected to a controller power supply unit 21. The gradient coils 11, 12 are energised by applying an electric current thereto by means of the power supply unit 21. The strength, direction and duration of the gradients are controlled by control of the power supply unit. The magnetic resonance imaging system also includes transmitter and receiver coils 13, 15 for generating RF excitation pulses and for picking up the magnetic resonance signals, respectively. The transmitter coil 13 is preferably constructed as a body coil 13 which is also referred to as a volume coil and enables enclosure of (a part of) the object to be examined. An MR control unit 20 controls the power supply unit and the transmitter and receiver coils so as to apply the gradient fields and RF excitation pulses and to pick up the magnetic resonance signals. The body coil is usually arranged in the magnetic resonance imaging system in such a manner that the patient 30 arranged in the magnetic resonance imaging system is situated within the body coil 13. The body coil 13 acts as a transmitter antenna for the transmission of the RF excitation pulses and RF refocusing pulses. The body coil 13 preferably involves a spatially uniform intensity distribution of the transmitted RF pulses. The same coil or antenna is usually used alternately as a transmitter coil and a receiver coil. Furthermore, the transmitter and receiver coil is usually shaped as a coil, but other geometries where the transmitter and receiver coil acts as a transmitter and receiver antenna for RF electromagnetic signals are also feasible. The transmitter and receiver coil 13 is connected to an electronic transmitter and receiver circuit 15.

It is to be noted, however, that it is alternatively possible to use separate receiver coils. For example, surface coils can be used as receiver coils. Such surface coils have a high sensitivity in a comparatively small volume. The transmitter coils, such as the surface coils, are connected to a demodulator 24 and the magnetic resonance signals (RFS) received are demodulated by the demodulator 24. The demodulated magnetic resonance signals (DMS) are applied to a reconstruction unit. The receiver coil is connected to a preamplifier 23. The preamplifier 23 amplifies the RF resonance signal (RFS) received by the receiver coil and the amplifier RF resonance signal is applied to a demodulator 24. The demodulator 24 demodulates the amplified RF resonance signal. The demodulated resonance signal contains the actual information concerning the local spin densities in the part of the object to be imaged. Furthermore, the transmitter and receiver circuit 15 is connected to a modulator 22. The modulator 22 and the transmitter and receiver circuit 15 activate the transmitter coil 13 so as to transmit the RF excitation and refocusing pulses. The reconstruction unit 25 derives one or more image signals, representing the image information of the imaged part of the object to be examined, from the demodulated magnetic resonance signals (DMS). In practice the reconstruction unit 25 is preferably constructed as a digital image processing unit 25 which is programmed to derive from the demodulated magnetic resonance signals the image signals which represent the image information of the part of the object to be imaged. The MR image signal (MR-im) on the output of the reconstruction unit 25 is applied to a combination unit 28 in order to combine it with the image information received on the basis of the detected ultrasound waves.

Further, the reconstruction unit 25 is programmed for correction of the preliminary ultrasound image on the basis of the magnetic resonance image. In particular the reconstruction unit 25 is provided with a segmentation algorithm to separate regions pertaining to different tissue types. A look-up-table is provided which assigns the proper values of the ultrasound sound velocity of respective tissue types to individual voxels or pixels in the magnetic resonance image. This look-up table is proved e.g. in the reconstruction unit 25 or in the combination unit 28. The reconstruction unit 25 is arranged to take the local ultrasound sound velocity as derived from the magnetic resonance image into account to reduce or avoid distortions in the ultrasound image. The reconstruction unit 25 is further programmed to extract tissue interfaces from the magnetic resonance image and relate US-signals to these tissue interfaces.

The diagnostic imaging system further comprises a position detection system which is arranged to detect the positions of the ultrasound transducer 110, the patient to be examined 30 and the position of the portion of the patient from where the magnetic resonance signals are obtained. The position detection system includes a camera-unit 201 and a number of markers in the form of LEDs or IREDs. LEDs or IREDs 202 are placed on the gantry of the magnetic resonance imaging system, further LEDs or IREDs 203 are placed on the ultrasound transducer 110 and LEDs or IREDs 204 are placed on the patient to be examined, at or near the region to be imaged. The camera-unit detects these LEDs or IREDs from various directions. The position detection system also has a position calculation system 205. The camera-unit 201 applies observation signals (OS) to the position calculation system 205. The observation signals (OS) represent the observations of the markers 202,203 and 204 from different directions. The position calculation unit computes the positions of the various markers from the observation signals and generates position signals (POS) representing the positions of the patient to be examined imaged in the (preliminary) ultrasound image and in the magnetic resonance image.

The ultrasound transducer is fitted with one or several micro-coils 210. In these micro-coils electrical induction signals (LS) are generated in response to the RF-excitations or gradient pulses. These electrical induction signals are position encoded due to the temporary read gradients and phase-encoding gradients and represent the position of the micro-coil 210. The electrical induction signals are processed in the same way as the magnetic resonance signals and the demodulator 24 derives an MR-position signal (mr-POS) that represents the position of the ultrasound transducer to the position calculation system 205. Thus, the position calculation system 205 is enabled to compute the position of the portion of the patient to be examined imaged in the (preliminary) ultrasound image from the MR-position signal (mr-POS). The position calculation system 205 computes the position of the micro-coil 210 from the MR-position signal (mr-POS) and supplies a position signal (POS) which represents the position of the micro-coil 210. The position signals (POS) from the position calculation system 205 are applied to the combination unit 28 to control the combination unit to combine image information from the magnetic resonance image and the (preliminary) ultrasound image according to their respective relative positions so that all image information is registered in a common reference frame.

The combination unit 28 is further arranged to correct the preliminary ultrasound image on the basis of distinguished tissue types and/or tissue interfaces in the magnetic resonance image. The combination unit generates the corrected ultrasound image in the form of the corrected image signal (C-im). The corrected ultrasound image is corrected for geometric distortions e.g. due to differences between ultrasound velocities in various types of tissues.

The ultrasound transducer 110 is mounted in or on the transmitter and receiver coil 13. The ultrasound transducer 110 is provided with the ultrasound probe 111. The ultrasound probe 111 produces the US detection signals (USS) in response to the ultrasound echoes which are received by the ultrasound probe and are generated in the patient to be examined when the ultrasound transducer generates ultrasound waves in the patient to be examined. The US detection signals are applied to a US processor 40. Such a US processor 40 is known per se from U.S. Pat. No. 5,795,297 and will be described in detail with reference to FIG. 2. The US processor forms, on the basis of the US detection signal and using a video processor 140, an US image signal (US-im) which is applied to a combination unit 28. The reconstruction unit 25 also applies the MR image signal (MR-im) to the combination unit 28. The combination unit derives a combined image signal (C-im) from the MR image signal and the US image signal (US-im). For example, a part of the signal levels of the US image signal and a part of the signal levels of the MR image signal are used in the combined image signal. It is alternatively possible to superpose, for example the image information contained in the US image signal on image information of the MR image signal as an overlay. In a particularly simple embodiment the combined image signal concerns an ultrasound image and a magnetic resonance image which are displayed on a monitor 26 adjacent one another or successively. For example, in this embodiment the combined image signal reproduces the functional information, such as instantaneous flow speeds of blood through the vascular system as represented by the US image signal, against the background of the anatomical information of said vascular system and its surroundings. This anatomical information faithfully reproduces small details, for example of the order of magnitude of from 0.5 mm to 2 mm. This anatomical information is represented by the MR image signal.

The magnetic resonance imaging system and the ultrasound system are controlled by a central control unit 50. The central control unit includes the US console 162 via which the user, for example the radiologist, can enter the parameters for the acquisition of the ultrasound image. The central control unit 50 also includes the MR console 163 via which the user can enter the parameters for the acquisition of the magnetic resonance image. The central control unit also includes a central control device 51 for controlling the ultrasound system and the magnetic resonance imaging system. To this end, the central control device 51 is coupled to the MR control unit 20 and to the US processor 40 via a data bus 60.

The combined image signal (C-im) is applied to a monitor 26 for the combined display of the ultrasound image and the magnetic resonance image thereon.

It is also possible to store the combined image signal in a buffer unit 27 while awaiting further processing.

Figure 2:
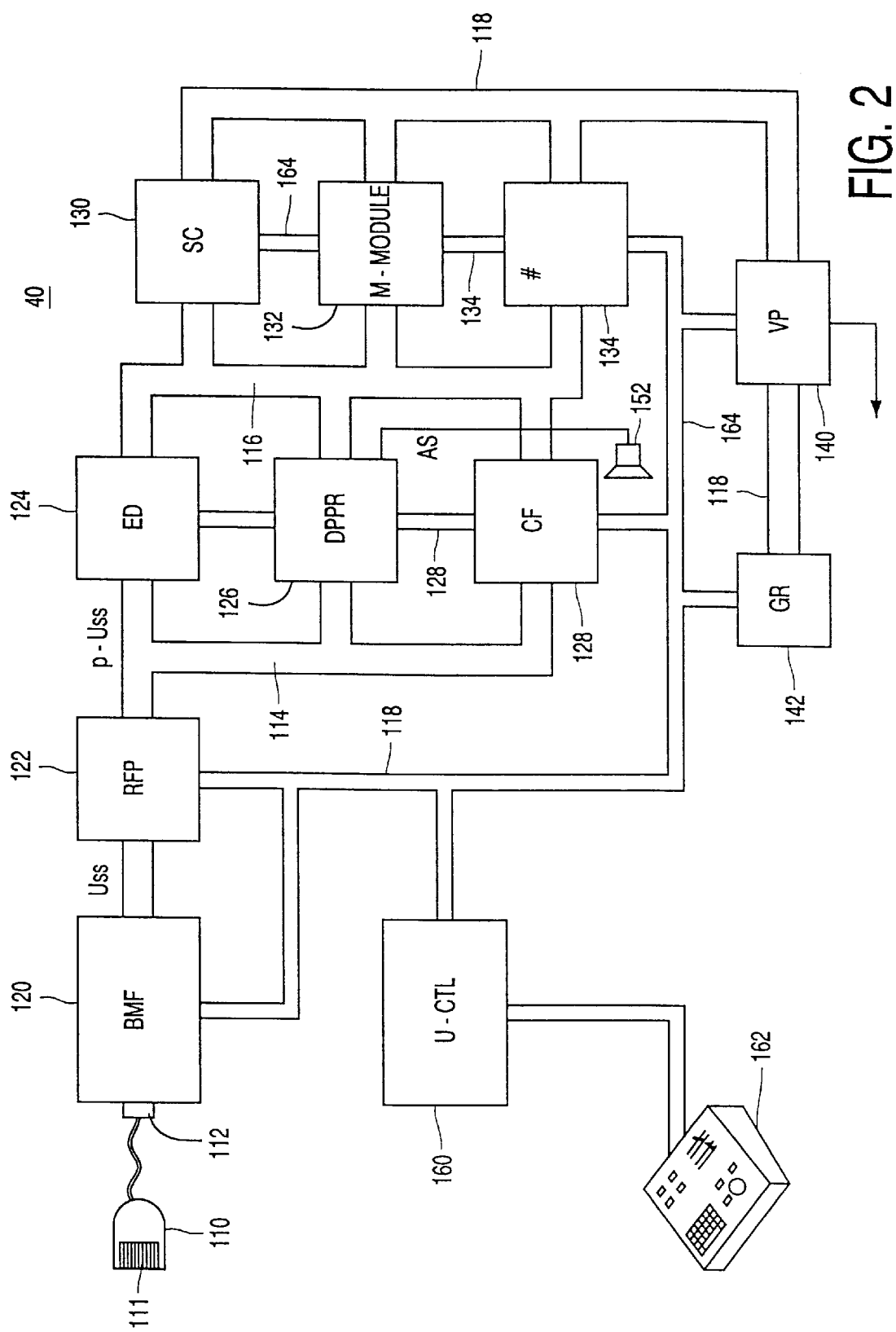
FIG. 2 shows diagrammatically the ultrasound system whose ultrasound probe is included in the receiver coil of the magnetic resonance imaging system of FIG. 1.

FIG. 2 shows diagrammatically the ultrasound system whose ultrasound probe is included in the receiver coil of the magnetic resonance imaging system shown in FIG. 1. The US detection signals (Uss) from the ultrasound probe 111 are processed by the ultrasound system with a number of electronic circuits. The ultrasound echoes from the patient to be examined, detected by the ultrasound probe, are processed directly and the information in the ultrasound echoes is visualised on the monitor 26. In the case of analogue processing of the US detection signal, the scanning of the patient to be examined by means of the ultrasound waves and the processing of the US detection signals are executed in synchronism, so that the (analogue) US detection signals are directly and continuously processed as soon as the ultrasound echoes are detected by the ultrasound probe.

FIG. 2 illustrates notably the modular architecture of the ultrasound system. The ultrasound probe 111, for example, an ultrasound probe of the linear type or of the phased array type, is connected to a beam-shaping module 120 which controls the excitation of the ultrasound waves and the reception of the ultrasound echoes. The ultrasound probe is provided with a large number of probe elements. Each of the ultrasound echoes originating from the patient to be examined reaches the individual probe elements at varying instants. The beam-shaping module provides the shaping of US detection signals (Uss) representing rays (or scanning lines) from the ultrasound echoes received. To this end, the beam shaping module delays the detection signals from the individual probe elements, so that the signal levels of the US detection signals are composed of detection signals from the probe elements which always relate to substantially the same positions within the patient to be examined; for example, detection signals are invariably taken along lines extending from the US transducer into the patient to be examined (so-called A-lines). The (RF) US detection signals (Uss) are applied to a post-processing module 122 which performs signal amplification and band-pass filtering. The processed US detection signals (p-Uss) are applied, via a first data bus 114, to the inputs of an echo detection module 124, of a Doppler module 126 and of a colour flow module 128. The echo detection module derives a two-dimensional (2D or B-mode or grey value) ultrasound image from the ultrasound echoes. In the B-mode the ultrasound image is composed of a plurality of successively taken A-lines. The Doppler module 126 derives Doppler signal estimates from the processed US detection signals and also a modulated audio signal (AS) which is applied to a loudspeaker 152. The Doppler shift of the ultrasound echoes is reproduced as sound via the loudspeaker, the pitch of the sound corresponding to the Doppler shift. Furthermore, US detection signals (p-Uss) processed by the colour flow module 128 are used to form colour components for a colour flow Doppler image rendition. The colour flow module forms a two-dimensional representation of the distribution of Doppler shifts of the ultrasound echoes; this representation is made, for example, in the form of a colour distribution. Thus, a colour image is formed in which the Doppler shifts are encoded on the basis of different colours, thus representing the speed distribution in the patient to be examined. The signal outputs of the echo detection module 124, of the Doppler module 126 and of the colour flow module 128 are connected to a number of imaging modules via a second data bus 116. The 2D signals of the echo detection module 124 are converted into a desired image format by the scan conversion module 130 and are converted into an M-mode display by an M-mode module 132. In the M-mode (motion mode) ultrasound echoes are repeatedly taken from a pre-selected A-line. The successive images of this A-line are consecutively and adjacently reproduced, so that an object moving through the relevant A-line is reproduced in motion. The M-module is also used to form a spectral representation of the signals produced by the Doppler modules 126; however, a separate spectral display module especially designed for this purpose may also be used. The signals produced by the colour flow module and the echo detection module can also be applied to the scan conversion module 130 where by they are combined so as to form a colour flow image of the desired format. The ultrasound system also includes a Cineloop® memory in which series of ultrasound images are stored. At a later stage the stored images can be reproduced again at the original image rate or in a decelerated fashion. The Cineloop® memory in the magnetic resonance imaging system according to the invention is preferably arranged to store, for playback at a later stage, also series of magnetic resonance images and/or series of combined images containing image information from magnetic resonance images and from ultrasound images.

The signals produced by the scan converter 130, the M-mode module 132 or the Cineloop® are applied to a video processor module 140 via a third data bus 118. The signal output of the video processor module 140 is connected to the combination unit 28 of the magnetic resonance imaging system. The video processor 140 supplies electronic video signals which are combined with the MR image signals (MR-im) by the combination unit 28. The electronic video signals from the video processor 140 represent the images formed by the various modules of the ultrasound system. The video processor 140 can also be used to add alphanumerical or graphic information to the ultrasound images. Examples in this respect are the name of the patient to be examined, scale indications or measuring results written on the ultrasound image by the user, that is, the radiologist. The graphic information is supplied by a graphics module 142 which is connected to the video processor 140 via the third data bus 118.

The modules of the ultrasound system are controlled by a system controller 160 which is accommodated in the central control unit 50 of the magnetic resonance imaging system. The system controller provides the interface with the US console 162 via which the user operates the ultrasound system. The user, that is, the radiologist, notably uses the US console to select a given ultrasound probe and a given imaging procedure. In response to the operation of the US console by the user, the system controller 162 provides commands for the beam shaping module 121 so as to load the necessary data of the ultrasound probe, to activate the ultrasound probe and to set the other modules for the processing of the information in the US detection signals (Uss) in conformity with the imaging procedure selected by the user. After the initialisation of the various modules, the system controller 160 remains inactive until the user enters new selections via the US console 162. Each of the individual modules of the ultrasound system includes a respective microprocessor for controlling and executing the function of the relevant module. The individual modules are constructed, for example, by means of one or more PCBs (printed circuit boards).

What is claimed is:

1. A diagnostic imaging system, notably a magnetic resonance imaging system comprising:
  a receiver antenna for picking-up magnetic resonance signals;
  an ultrasound probe for receiving ultrasound echoes; and
  a reconstruction unit for reconstructing a diagnostic image from the magnetic resonance signals and the ultrasound echoes, the reconstruction unit combining the magnetic resonance signals and the ultrasound echoes to form a combined image corresponding to the diagnostic image,
  wherein the reconstruction unit is further configured to reconstruct a magnetic resonance image from the magnetic resonance signals, reconstruct a preliminary ultrasound image from the ultrasound echoes, and derive the diagnostic image from the preliminary ultrasound image and the magnetic resonance image,
  wherein the reconstruction unit is still further configured to register the magnetic resonance image and the preliminary ultrasound image with respect to one another in a common coordinate system, and derive the diagnostic image from the registered resonance image and the registered ultrasound image, and
  wherein the reconstruction unit is still further configured to correct the preliminary ultrasound image on the basis of the magnetic resonance image so as to form a corrected ultrasound image as the diagnostic image.

2. The diagnostic imaging system as claimed in claim 1, wherein the reconstruction unit is further configured to:
  derive local tissue types from the magnetic resonance image;
  derive local ultrasound sound-velocities from the local tissue types; and
  correct the preliminary ultrasound image on the basis of the local ultrasound sound-velocities.

3. The diagnostic imaging system as claimed in claim 1, wherein the reconstruction unit is further configured to identify anatomical landmarks from the preliminary ultrasound image and from magnetic resonance image respectively.

4. The diagnostic imaging system as claimed in claim 1, wherein the reconstruction unit is further configured to:
  measure the position of the ultrasound probe in response to the magnetic resonance signals; and
  register the preliminary ultrasound image with respect to the magnetic resonance image on the basis of the measured position of the ultrasound probe.

5. The diagnostic imaging system as claimed in claim 4, wherein the ultrasound probe is provided with MR-susceptible markers or mini-coils.

6. The diagnostic imaging system as claimed in claim 1 wherein the ultrasound probe is coupled to the receiver antenna, the ultrasound probe for detecting ultrasound waves; and
  the magnetic resonance imaging system further comprising a display system for the combined display of information contained in the magnetic resonance signals and information contained in the ultrasound waves.

7. The magnetic resonance imaging system as claimed in claim 6, wherein the display system is configured to reproduce an image with brightness values derived from the magnetic resonance signals and with brightness values derived from the ultrasound waves.

8. The magnetic resonance imaging system as claimed in claim 6, wherein the display system is configured to display alternately image information derived from the magnetic resonance signals and image information derived from the ultrasound waves.

9. The magnetic resonance imaging system as claimed in claim 6, wherein the display system is configured to display in superposed form image information derived from the magnetic resonance signals and image information derived from the ultrasound waves.

10. The magnetic resonance imaging system as claimed in claim 6, wherein the display system is further configured to:
   acquire a value of a physical quantity in a measuring position from the ultrasound waves;
   reconstruct a magnetic resonance image from the magnetic resonance signals; and
   reproduce the acquired value of the physical quantity in the magnetic resonance image in a position in the magnetic resonance image which corresponds to the measuring position.

11. A computer program comprising instructions for:
   picking-up magnetic resonance signals;
   receiving ultrasound echoes; and
   reconstructing a diagnostic image from the magnetic resonance signals and the ultrasound echoes by combining the magnetic resonance signals and the ultrasound signals to form a combined image corresponding to the diagnostic image,
   wherein reconstructing further includes reconstructing a magnetic resonance image from the magnetic resonance signals, reconstructing a preliminary ultrasound image from the ultrasound echoes, and deriving the diagnostic image from the preliminary ultrasound image and the magnetic resonance image,
   wherein reconstructing still further includes registering the magnetic resonance image and the preliminary ultrasound image with respect to one another in a common coordinate system, and deriving the diagnostic image from the registered resonance image and the registered ultrasound image, and
   wherein reconstructing still further includes correcting the preliminary ultrasound image on the basis of the magnetic resonance image so as to form a corrected ultrasound image as the diagnostic image.

* * * * *